United States Patent [19]

Labroo et al.

[11] Patent Number: 5,710,244

[45] Date of Patent: Jan. 20, 1998

[54] DERIVATIZED CALCITONINS

[76] Inventors: Virender M. Labroo, 2814 163rd Pl. SE., Mill Creek, Wash. 98012; Tomikazu Sasaki, 762 Hayes St. #16, Seattle, Wash. 98109

[21] Appl. No.: 176,153

[22] Filed: Dec. 30, 1993

Related U.S. Application Data

[63] Continuation-in-part of Ser. No. 999,749, Dec. 31, 1992, abandoned.

[51] Int. Cl.$^6$ .................... A61K 38/23; C07K 14/585
[52] U.S. Cl. .................... 530/307; 514/6; 514/12; 514/808
[58] Field of Search .................... 514/12, 6, 808; 530/307

[56] References Cited

U.S. PATENT DOCUMENTS

| | | | |
|---|---|---|---|
| 3,798,203 | 3/1974 | Brugger et al. | 260/112.5 |
| 3,956,260 | 5/1976 | Brugger et al. | 260/112.5 |
| 4,650,854 | 3/1987 | Neiss et al. | 530/307 |
| 4,758,550 | 7/1988 | Cardinaux et al. | 514/12 |
| 4,764,589 | 8/1988 | Orlowski et al. | 530/307 |
| 4,820,804 | 4/1989 | Orlowski et al. | 530/307 |
| 4,824,936 | 4/1989 | Orlowski et al. | 530/307 |
| 5,001,222 | 3/1991 | Orlowski et al. | 530/307 |
| 5,010,174 | 4/1991 | Hirose et al. | 530/307 |
| 5,175,146 | 12/1992 | Basava et al. | 514/12 |

FOREIGN PATENT DOCUMENTS

| | | |
|---|---|---|
| 297159 | 7/1987 | European Pat. Off. . |
| 370165 | 7/1989 | European Pat. Off. . |
| 1259870 | 1/1972 | United Kingdom . |
| 88/02756 | 4/1988 | WIPO . |

OTHER PUBLICATIONS

Rittel et al., *Experientia* 32 (2): 246–248, 1976.
Liu et al., "The Stereochemistry of Complex Inorganic compounds. XXVII. Asymetric Syntheses of Tris(bypyridine)Comlexes of Ruthenium(II) and Osmium(II)", Inorganic Chemistry, vol. 3, No. 8, Jul. 1964.
Lieberman et al., "Iron(II) Organizes a Synthetic Peptide into Three–Helix Bundles", Am. Chem. Soc., 113(4) (1991), pp. 1470–1471 1991.
Saito et al., *J. Pharma. Sci.* 74:345–347, 1985.
Mosley et al., *J. Biol. Chem.* 257: 5846–5851, 1982.
Yates et al., *Endocrinology* 126: 2845–2849, 1990.

Primary Examiner—Elizabeth C. Weimar
Assistant Examiner—Anish Gupta

[57] ABSTRACT

Derivatized calcitonin molecules, pharmaceutical compositions comprising derivatized calcitonins, and methods of reducing serum calcium in a patient using the derivatized calcitonins are disclosed. The molecules are characterized by a derivatized amino terminus formed by combining a calcitonin with a cyclic, polycyclic or heterocyclic moiety. Multimeric forms of the molecules are also disclosed.

26 Claims, 2 Drawing Sheets

DERIVATIZED CALCITONINS

CROSS-REFERENCE TO RELATED APPLICATION

The present application is a continuation-in-part of Ser. No. 07/999,749, filed Dec. 31, 1992, which application is incorporated herein by reference now abandoned.

BACKGROUND OF THE INVENTION

Bone is a dynamic tissue, and homeostasis in the adult skeleton requires a balance between the formation of new bone and the resorption of previously formed bone. Calcitonin, a peptide hormone secreted by the thyroid and thymus of mammals, plays an important role in maintaining bone homeostasis. Calcitonin binds to receptors found on osteoclasts, cells in the bone tissue which mediate bone resorption. Calcitonin immobilizes the osteoclast, thus inhibiting bone resorption with a resultant decrease in the amount of calcium released by bone into the serum. This inhibition of bone resorption has been exploited by using calcitonin as a treatment for osteoporosis.

Calcitonin occurs in the thyroid glands of mammals and the ultimobranchial glands of lower vertebrates. Known, naturally occurring calcitonins are all 32-amino acid polypeptides having an amidated carboxy terminus and an intramolecular disulfide bond between cysteine residues in the 1 and 7 positions.

At the present time, salmon calcitonin is preferred over human calcitonin for treatment of osteoporosis. The worldwide market for salmon calcitonin exceeds $500 million annually. Salmon calcitonin has been shown to be considerably more effective in arresting bone resorption than human forms of calcitonin. There are several hypotheses for why salmon calcitonin is more potent than human calcitonin in treatment of osteoporosis. These hypotheses include: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites.

Despite the advantages associated with the use of salmon calcitonin for treatment of osteoporosis in humans, there are also disadvantages. Salmon calcitonin is administered by injection, a process that many patients find unacceptable. In addition, some patients develop antibodies to non-human calcitonin. Therefore, new analogs of salmon, human or other calcitonins that are potent inhibitors of bone resorption, less expensive, more convenient to administer and non-immunogenic are needed.

SUMMARY OF THE INVENTION

It is an object of the present invention to provide novel calcitonin derivatives that have enhanced hypocalcemic activity and/or extended in vivo half-life.

It is a further object of the invention to provide pharmaceutical compositions comprising novel calcitonin derivatives, as well as methods of reducing serum calcium in patients by administration of the pharmaceutical compositions.

Within one aspect, the present invention provides compounds selected from the group consisting of R-CONH-Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH$_2$ (Sequence ID Number 1), $$\text{S}\text{———}\text{S}$$
$$|\qquad\qquad\quad|$$

R-CONH-Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH$_2$ (Sequence ID Number 2), and pharmaceutically acceptable salts thereof, wherein R is substituted or unsubstituted biaryl, optionally containing 1 or 2 ring nitrogen atoms per ring; substituted or unsubstituted heterocycloalkyl containing 1 or 2 ring heteroatoms per ring selected from the group consisting of N, S and O; substituted or unsubstituted bis-heterocycloalkyl containing 1 or 2 heteroatoms per ring selected from the group consisting of N, S and O; or substituted or unsubstituted heteroaryl containing 1 to 4 heteroatoms per ring selected from the group consisting of N, S and O.

Within another aspect, the present invention provides compounds of the formula R-N-CT, wherein CT is a calcitonin selected from the group consisting of human, salmon, eel, rat, porcine, bovine, ovine and chicken calcitonins and biologically active derivatives and variants thereof, or a pharmaceutically acceptable salt thereof; N is an amide linkage; and wherein R is substituted or unsubstituted biaryl, optionally containing 1 or 2 ring nitrogen atoms per ring; substituted or unsubstituted heterocycloalkyl containing 1 or 2 ring heteroatoms per ring, selected from the group consisting of N, S and O; substituted or unsubstituted bis-heterocycloalkyl containing 1 or 2 heteroatoms per ring selected from the group consisting of N, S and O; or substituted or unsubstituted heteroaryl containing 1 to 4 heteroatoms per ring selected from the group consisting of N, S and O.

Within a third aspect, the present invention provides compounds of the formula X-(R-N-CT)$_n$ wherein X is an ion of a transition metal; R is a heterocycloalkyl or heteroaryl group; CT is a calcitonin selected from the group consisting of human, salmon, eel, rat, porcine, bovine, ovine and chicken calcitonins and biologically active derivatives and variants thereof; N is an amide linkage; and n=2 or 3. Pharmaceutically acceptable salts of these compounds are also provided.

The compounds disclosed above are combined with a pharmaceutically acceptable carrier to produce pharmaceutical compositions. These compositions are useful for, inter alia, reducing serum calcium in a patient.

LIST OF ABBREVIATIONS

DMSO Dimethylsulfoxide

BHA Benzhydrylamine

MBHA 4-methylbenzhydrylamine

FMOC 9-fluorenylmethoxycarbonyl

BOC t-butyloxycarbonyl

Trit Trityl

Bu$^t$ t-butyl

PMC 2,2,5,7,8-pentamethylchroman-6-sulfonyl

BOP Benzotriazolyl-N-oxytrisdimethylaminophosphonium hexafluorophosphate

PyBOP Benzotriazole-1-yl-oxy-tris-pyrrolidino phosphonium hexafluorophosphate

PyBrOP Bromo-tris-pyrrolidino-phosphonium hexafluorophosphate
HBTU [2-(1H-benzotriazole-1-yl)1,1,3,3,-tetramethyl uronium hexafluorophosphate
HOBt 1-hydroxybenzotriazole
DIEA Diisopropylethyl amine
Et₃N Triethylamine
DMF Dimethylformamide
NMP N-methylpyrrolidone
HPLC High performance liquid chromatography
AAA Amino acid analysis
DCM Methylene chloride
SCT Salmon calcitonin
TFA trifluoroacetic acid
DIC Diisopropyl-carbodiimide
DCC dicyclohexylcarbodiimide
FAB-MS Fast Atom Bombardment—Mass Spectroscopy

DETAILED DESCRIPTION OF THE INVENTION

The present invention provides new derivatized calcitonin molecules. These molecules are provided in both monomeric and multimeric forms. The derivatized calcitonins of the present invention provide various advantages over currently available calcitonins, including higher specific activity, increased half-life, increased stability and/or reduced immunogenicity.

The derivatized calcitonins of the present invention include derivatized human, salmon, eel, rat, porcine, bovine, ovine and chicken calcitonins. Salmon and, in particular, human calcitonins are preferred. The calcitonins may be derived from the native, wild-type molecules or may be derived from modified forms of calcitonin having biological activity. A variety of modified calcitonins are known in the art, including calcitonins having amino acid substitutions (e.g. U.S. Pat. Nos. 4,824,936; 4,764,589; 4,663,309 and 4,658,014), deletions (e.g. U.S. Pat. Nos. 4,820,804; 4,764,591; 4,639,511; 4,605,514 and 4,537,716) and calcitonins containing D-amino acid substitutions (U.S. Pat. No. 4,652,627). The term "biologically active" is used herein to denote calcitonins that exhibit bone resorption inhibiting activity. Hypocalcemic activity and receptor-mediated stimulation of cAMP are indicators of bone resorption inhibiting activity of calcitonins.

The molecules of the present invention are characterized by a derivatized amino terminus, formed by combining a calcitonin with a cyclic, polycyclic or heterocyclic moiety selected from the group consisting of substituted or unsubstituted biaryl, optionally containing 1 or 2 ring nitrogen atoms per ring; substituted or unsubstituted heterocycloalkyl containing 1 or 2 ring heteroatoms per ring selected from the group consisting of N, S and O; substituted or unsubstituted bis-heterocycloalkyl containing 1 or 2 heteroatoms per ring selected from the group consisting of N, S and O; and substituted or unsubstituted heteroaryl containing 1 to 4 heteroatoms per ring selected from the group consisting of N, S and O, wherein the cyclic, polycyclic or heterocyclic moiety is joined to the N-terminal cysteine residue of the calcitonin via an amide linkage. Thus, within one aspect of the present invention, a calcitonin is reacted with a carboxylic acid of one of the above-described moieties to yield an N-terminal derivatized calcitonin.

As used herein, the terms cyclic, polycyclic, heterocyclic, heterocycloalkyl and equivalents thereof are used to denote ring structures having three or more atoms per ring. In general, these structures will have fewer than nine atoms per ring, preferably five, six or seven atoms per ring, although structures containing twelve or more ring atoms may be used. The terms biaryl, heteroaryl and equivalents thereof are used to denote aromatic ring structures having five or more atoms per ring, preferably five to eight ring atoms, more preferably five or six ring atoms per ring.

Within the present invention, the cyclic, polycylic, and heterocyclic moieties include fused ring structures containing from 2-3 rings per fused ring group. Preferred fused ring structures include biaryl moieties having the structure wherein X, $X_1$, $X_2$, $X^3$, Y, $Y_1$, $Y_2$ and $Y_3$ are individually C or N and R' is linear $C_1$–$C_8$ alkyl, branched $C_1$–$C_{12}$ alkyl, nitro, hydroxyl, carboxyl, trifluoromethyl, carboxylamide, sulfhydryl, cyano, halo, alkoxy, ester or H.

A second group of preferred fused ring structures includes the structure wherein $X_4$ and $Y_4$ are individually C, N, O or S, $X_5$, $X_6$, $Y_5$ and $Y_6$ are individually C or N subject to the limitations that when $X_4$ is S or O, $X_5$ must be C and when $Y_4$ is S or O, $Y_5$ must be C and R' is as defined above. A third group of preferred fused ring structures includes heterocycloalkyl moieties having the structure wherein X is N, O or S; Y is C or N; n=1 or 2; and R' is as defined above. A fourth group of preferred fused ring structures includes bis-heterocycloalkyl moieties having the structure wherein X, $X_1$, Y and $Y_1$ are individually N, O or S and R' is as defined above. A fifth group of preferred fused ring structures includes heteroaryl moieties having the structure or the structure wherein X is C, O, S or N; Y, Z and A are individually C or N and R' is as defined above.

A preferred class of calcitonin derivatives includes those modified by the addition of a compound of the formula:

wherein $X_1$ and $Y_1$ are individually C or N and R' is linear $C_1$–$C_8$ alkyl, branched $C_1$–$C_{12}$ alkyl, nitro, hydroxyl, trifluoromethyl, carboxyl, carboxylamide, sulfhydryl, cyano, halo, alkoxy, ester or H. Particularly preferred members of this class include those modified by the addition of the compounds:

A second preferred class of calcitonin derivatives includes those modified by the addition of a compound of the formula:

wherein n=1 or 2, $X_2$ is N, O or S, $Y_2$ is C or N and R' is as defined above. Particularly preferred members of this class include those modified by the addition of the compound:

A third preferred class of calcitonin derivatives includes those modified by the addition of a compound of the formula:

wherein $X_3$ and $Y_3$ are individually N, O or S, and R' is as defined above. Particularly preferred members of this class include those modified by the addition of the compound:

A fourth preferred class of calcitonin derivatives includes those modified by the addition of a compound of the formula:

wherein $Y_4$ is O, S or N; $X_4$, Z and A are individually C or N, subject to the limitation that $X_4$ is not N when $Y_4$ is O or S; and R' is as described above. Particularly preferred members of this class include those modified by the addition of the compounds:

A fifth preferred class of calcitonin derivatives includes those modified by the addition of a compound of the formula:

wherein $X_5$ is N, $Y_5$ is C or N, and R' is as described above. Particularly preferred members of this class include those modified by the addition of the compounds:

A sixth preferred class of calcitonin derivatives includes those modified by the addition of a compound of the formula:

wherein $X_5$ is N, $Y_5$ is C or N, and R' is as described above.

Within the compounds described above, those in which R' is $CO_2H$ or H are particularly preferred.

The calcitonin derivatives of the present invention can be synthesized by solid phase or solution phase methods conventionally used for the synthesis of peptides (see, for example, Merrifield, R. B. *J. Amer. Chem. Soc.* 85.: 2149–2154, 1963; Birr, C. *Aspects of the Merrifield Peptide Synthesis*, Springer-Verlag, Heidelberg, 1978; Carpino, L. A., *Acc. Chem. Res.* 6:191–198, 1973; Kent S. B., *Ann. Rev. Biochem.* 57:957–989, 1988; Gregg et al. *Int. J. Peptide Protein Res.* 35:161–214, 1990; *The Peptides, Analysis, Synthesis, Biology*, Vol. 1, 2, 3, 5: Gross, E. and Meinhofer, J. eds., Acad. Press, New York, 1979; and Stewart et al., *Solid Phase Peptide Synthesis*, 2nd. ed. Pierce Chem. Co., Rockford, Ill., 1984; which are incorporated herein by reference in their entirety.) The use of solid phase methodology is preferred. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization (in the case of BOC chemistry, vide infra) and coupling of successive protected amino acid derivatives are used to link the amino acids from the C-terminus according to the amino acid sequence. Preferred solid supports are divinylbenzene cross-linked polystyrene resins, which are commercially available in a variety of functionalized forms, including chloromethyl resin, hydroxymethyl resin, paraacetamidomethyl resin, benzhydryl amine (BHA) resin, p-methylbenzhydrylamine (MBHA) resin, oxime resins, 4-alkoxybenzyl alcohol resin, 4-(2',4'-dimethoxyphenylaminomethyl)-phenoxymethyl resin, 2,4-dimethoxybenzhydrylamine resin, and 4-(2',4'-dimethoxyphenyl-FMOC-aminomethyl)-phenoxyacetamidonorleucyl-MBHA resin (Rink amide MBHA resin). BHA, MBHA and Rink amide MBHA resins are particularly preferred, since they can directly provide C-terminal amides after cleavage of the peptide chain from the resin. A particularly preferred resin for use within the present invention is the Rink amide MBHA resin (available from Nova Biochem, La Jolla, Calif.). A preferred protecting group for the α-amino group of the amino acids is acid-labile t-butyloxycarbonyl (BOC). BOC is deprotected using trifluoroacetic acid (TFA) in a suitable solvent, such as methylene chloride. The resultant TFA salt is neutralized with a base, such as diisopropylethyl amine (DIEA) or triethylamine ($Et_3N$), then coupled with the protected amino acid derivative. Another preferred protecting group for α-amino acids is base-labile 9-fluorenylmethoxycarbonyl (FMOC). Suitable protecting groups for the side chain functionalities of amino acids chemically compatible with BOC and FMOC groups are well known in the art. When using FMOC chemistry, the following protected amino acid derivatives are preferred: FMOC-Cys(Trit), FMOC-Ser (But), FMOC-Asn(Trit), FMOC-Leu, FMOC-Thr(Trit), FMOC-Val, FMOC-Leu, FMOC-Gly, FMOC-Lys(Boc), FMOC-Gln(Trit), FMOC-Glu(OBut), FMOC-His(Trit), FMOC-Tyr(But), FMOC-Arg(PMC), and FMOC-Pro. The amino acid residues can be coupled by using a variety of coupling agents and chemistries known in the art, such as direct coupling with DIC, DCC or BOP; via preformed symmetrical anhydrides; via active esters such as pentafluorophenyl esters; or via preformed HOBt active esters. Activation with HBTU ([2-(1H-Benzotriazole-1-yl), 1,1,3,3-tetramethyluronium hexafluorophosphate]) in the presence of hydroxybenzotriazole (HOBt) is preferred.

The solid phase method can be carried out manually, although automated synthesis on a commercially available peptide synthesizer (e.g. Applied Biosystems 431A or the like) is preferred. In a typical synthesis, FMOC-Rink-amide MBHA resin is treated with 20% piperidine in NMP to remove the FMOC group. After washing the resin with NMP, the first amino acid (the C-terminal FMOC-Pro) is loaded on the resin using the HBTU/HOBt method. Successive deprotection (with 20% piperidine/NMP) and coupling cycles according to ABI FastMoc protocols (ABI user bulletins 32 and 33, Applied Biosystems Inc.) are used to build the whole peptide sequence.

Before attaching the N-terminal modifying group, the identity and integrity of the peptide are established, such as by deprotecting and cleaving a small portion of the FMOC-peptide resin with Reagent K (0.75 g cystalline phenol, 0.25 ml ethanedithiol, 0.5 ml thioanisole, 0.5 ml dionized water, 10 ml TFA) or the like. The peptide is precipitated and washed with ether, purified by reverse phase HPLC and characterized by amino acid analysis and mass spectroscopy.

The amino terminus of the calcitonin is then derivatized. When using FMOC chemistry, the N-terminal FMOC group of the peptide resin is typically deprotected with 20% piperidine in DMF for 20–30 minutes. The resin is filtered, washed thoroughly with DMF and DCM, and dried. The carboxylic derivatives to be used for N-terminal modification (to introduce R groups) can be coupled to the N-terminal amino group of the resin-linked peptide by the same activating procedures used in peptide synthesis, such as carbodiimide-mediated coupling; mixed anhydride; symmetrical anhydride; preformed active ester; acyl chloride; BOP, PyBOP, or pyBrOP-mediated coupling with or without HOBt; or variations and improvements thereof known in the art (see, for example, Coste et al., *Tetrahedron Lett.* 31: 669, 1990 and Coste et al., *Tetrahedron Lett.* 31: 205, 1990). Coupling can be done manually or by automated means. A particularly preferred method is to first pre-activate the carboxylic acid derivative by reacting it with HOBt and DIC in a mixture of DCM and DMF at room temperature to form the HOBt ester of the carboxylic acid derivative. This mixture is then added to the deprotected peptide-resin, and the suspension is shaken at room temperature. The reaction is followed by Kaiser test. The resin is then filtered, washed with DMF and DCM, and dried.

The derivatized peptide is cleaved from the resin and deprotected by treatment with TFA containing appropriate scavengers. Many such cleavage reagents, such as reagent K and others, may be used. The modified peptide is separated from the resin by filtration and isolated by ether precipitation. Further purification may be achieved by conventional methods such as gel filtration and reverse phase HPLC.

The disulfide bond between the two cysteines at positions 1 and 7 of calcitonin is formed according to conventional methods, such as by aerial oxidation or oxidation with potassium ferricyanide or DMSO (Tam et al. *J. Am. Chem. Soc.* 113:6657–6662, 1991). A particularly preferred method is oxidation with DMSO. After the oxidation reaction is complete, as monitored by HPLC or Ellman's reagent, the peptide is isolated and purified by HPLC and analyzed for purity by analytical HPLC and mass spectrometry.

Within another aspect of the invention, multimeric calcitonins are provided. A calcitonin derivatized with a heterocycloalkyl or heteroaryl group is combined with an ion of a transition metal to form a complex. Preferred calcitonin derivatives in this regard are those modified by the addition of a linear bicyclic moiety containing two ring nitrogen atoms, such as a bipyridine or bipyridine-like moiety. For example, salmon calcitonin derivatized with dicarboxy-bipyridine forms a 3:1 molar complex with $Fe^{2+}$. Other metals useful in this regard include $Cr^{3+}$, $Fe^{3+}$, $Mn^{2+}$, $Co^{2+}$, $Co^{3+}$, $Ni^{2+}$, $Cu^{2+}$, $Cu^+$ and $Zn^{2+}$. A preferred method for preparing complexes is by titration of modified calcitonins with an aqueous solution of an appropriate metal salt.

Calcitonin derivatives according to the present invention may be in the form of pharmaceutically acceptable salts, especially acid-addition salts including salts of organic acids and mineral acids. Examples of such salts include salts of organic acids such as formic acid, acetic acid, propionic acid, glycolic acid, lactic acid, pyruvic acid, oxalic acid, succinic acid, malic acid, tartaric acid, citric acid, benzoic acid, salicylic acid and the like. The acid-addition salts of the basic amino acid residues are prepared by treatment of the peptide with the appropriate acid or mineral according to procedures well known to those skilled in the art, or the desired salt may be obtained directly by lyophilization out of the appropriate acid.

The compounds of the present invention have hypocalcemic activity and are useful within human and veterinary medicine for the reduction of serum calcium and regulation of bone metabolism. The compounds of the present invention may be used, for example, in the treatment of osteoporosis, Paget's disease, hyperparathyroidism, osteomalacia, idiopathic hypercalcemia of infancy and other conditions. The calcitonin derivatives can also be used to inhibit gastric secretion in the treatment of acute pancreatitis and gastrointestinal disorders.

Pharmaceutical compositions are administered at daily to weekly intervals. An "effective amount" of such a pharmaceutical composition is the amount that provides a clinically significant reduction in serum calcium, inhibition of bone resorption, inhibition of gastric secretion or other effect. Such amounts will depend, in part, on the particular condition to be treated, age, weight, and general health of the patient, and other factors evident to those skilled in the art. The concentration of therapeutically effective doses of the calcitonin derivatives can vary widely depending on the indication and are well known in the art. For example, therapeutic doses for the treatment of osteoporosis generally range from 50–150 International Units (I.U.). Potency is estimated by comparing the hypocalcemic effect in rats with that of a standard preparation and is expressed in International Units, as described in the International Reference of Preparation, distributed by the National Institute for Biological Standards and Control, Holly Hill, London. Compounds having significantly enhanced half-lives may be administered at lower doses.

The calcitonin derivatives and their pharmaceutically acceptable salts are formulated with a pharmaceutically acceptable carrier for parenteral, oral, nasal, rectal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, tablets, etc. One skilled in this art may formulate the compounds of the present invention in an appropriate manner, and in accordance with accepted practices, such as those disclosed in *Remington's Pharmaceutical Sciences*, Gennaro, ed., Mack Publishing Co., Easton, Pa., 1990 (which is incorporated herein by reference in its entirety).

The following examples are offered by way of illustration, not limitation.

EXAMPLE 1

A. Synthesis of Salmon Calcitonin

Linear protected salmon calcitonin (SCT) was synthesized by solid phase methodology on an Applied Biosystems, Inc. (Foster City, Calif.) 431A peptide synthesizer using FMOC chemistry and HOBt and HBTU activation methodology. Rink amide MBHA resin (Nova Biochem, La Jolla, Calif.) with 0.43 mM substitution (580 mg) was used. All the couplings were >98.5 %. At the end of the synthesis the resin was thoughly washed with NMP and $CH_2Cl_2$ and dried. A small portion (27 mg) of the resin-linked FMOC-SCT was deprotected and cleaved in 10 ml of reagent K for 2.5 hr. The resin was filtered and solution evaporated. The residue was chromatographed on a Vydac C-4 (2.2×25 cm) HPLC column using a gradient of 0–60% B in 40 minutes (Solvent A: 0.1% TFA in water and Solvent B: 0.1% TFA in acetonitrile) to provide pure FMOC-SCT. Retention time of the peptide was 36.38 min. The peptide was characterized by amino acid analysis and mass spectometry (ms 3656.33) to establish the integrity of the salmon calcitonin link to the resin.

B. Preparation of Bipyridine-modified Calcitonin (ZP-1 or $BP_{4,4}$-CT)

2,2'-Bipyridine-4,4'-dicarboxylic acid (0.2 mM) was dissolved in 3 ml of 5% diisopropylethylamine (DIEA) in $CH_2Cl_2$ in a flask equipped with a stir bar and drying tube. N-Hydroxybenzotriazole (HOBt) (0.5 mM) and diisopropylcarbodiimide (DIC) (0.5 mM) were added to form the HOBt diester; after 45 minutes of stirring, the solution had cleared and turned faint yellow. SCT-resin (100 mg) was treated with 20% piperidine in DMF to remove the N-terminal protecting group. The deprotected SCT-resin was added to the solution of 2,2'-bipyridine carboxylic acid HOBt diester. The mixture was kept shaking overnight. A negative Kaiser test for free $NH_2$ group indicated that coupling was complete. The SCT-resin was washed with DMF and $CH_2Cl_2$.

The reduced form of bipyridine-modified SCT was cleaved from the resin with reagent K, and purified by reverse phase HPLC. A mixture of acetonitrile and water containing 0.1% trifluoroacetic acid was used as HPLC solvent. A linear gradient (20% $CH_3CN$/water to 80% $CH_3CN$/water in 20 minutes) was used to elute the peptide. The major peak was collected and lyophilized. The resulting peptide was oxidized by first dissolving the peptide in 1% aqueous ammonium bicarbonate solution containing 14% DMSO, at peptide concentration of 5 mg/ml. After the mixture was held overnight at room temperature the product was isolated and purified by reverse phase HPLC. The yield was 15 mg. The purified peptide was characterized using mass spectroscopy and AAA. FAB-MS gave m/e=3660 (MH+). AAA gave Asx 2.20 (2), Glx 3.43 (3), Ser 4.16 (4), Gly 3.38 (3), His 0.98 (1), Arg 1.19 (1), Thr, 4.96 (5), Pro 2.24 (2), Tyr 1.21 (1), Val 1.00 (1), Cys 0.86 (2), Leu 4.54 (5), Lys 2.22 (2).

Circular dichroism spectroscopy was used to study the conformation of the calcitonin derivatives and their Fe(II) complexes in aqueous buffer solution. The apparent molecular weight of bipyridine modified calcitonins was determined by gel-filtration and sedimentation equilibrium experiments in the presence and absence of Fe(II). The formation constants and dissociation rates of the trimeric calcitonin-Fe(II) complexes was determined by UV spectroscopy.

C. Preparation of Nicotinic acid-modified Calcitonin (ZP-5 or Nic-SCT)

Nicotinic acid ($3.7 \times 10^{-5}$ mol) was dissolved in a few drops of DMF. DIC ($3.7 \times 10^{-5}$ mol) was then added. The mixture was shaken at room temperature for approximately 10 minutes, after which the deprotected SCT-resin was added. The coupling reaction was followed using the Kaiser Test. The suspension was shaken overnight.

The Nic-SCT was cleaved from the resin by mixing reagent K (1.65 ml TFA, 0.112 ml 88% phenol, 0.098 ml $H_2O$, 0.1 ml thioanisole, 0.05 ml ethanedithiol) with the Nic-SCT resin. The reaction mixture was shaken at room temperature for 2.5 hours, and then the mixture was filtered to remove the resin. The peptide was precipitated in cold ether, and collected by centrifugation. The precipitate was washed with ether three times and dried in a dessicator for approximately one hour. The dried peptide was dissolved in 0.5 ml $H_2O$ and then applied to a Sephadex G-15 column. The column was eluted with 5% acetic acid. The peptide was detected by absorbance at 270 nm. Fractions containing the peptide were pooled and lyophilized.

The Nic-SCT was analyzed by reversed phase HPLC using a $C_4$-analytical column (Vydac, Hesperia, Calif.). The HPLC was monitored at 270 nm. The eluant was acetonitrile and water containing 1% TFA. A linear gradient, from 20% to 80% acetonitrile in 20 minutes, was used to elute the Nic-SCT. The major peak (55% acetonitrile) was collected and lyophilized. The total amount of peptide was approximately 18 mg.

The Nic-SCT (18 mg) was oxidized with DMSO to form an intramolecular disulfide bond. The disappearance of the reduced from of Nic-SCT was followed by Ellman's reagent. The inital concentration was 2 mg/ml in buffer solution (2% $NH_4HCO_3$, pH 8.0) containing 10% DMSO. The mixture was stirred overnight. The HPLC of the oxidized Nic-SCT showed a single peak, and the retention time (59% acetonitrile) was longer than that of the reduced form (55% acetonitrile). The oxidized Nic-SCT was found to be >95% pure based on HPLC. The total amount of pure peptide was 17 mg.

D. Preparation of Pycolinyl-modified Calcitonin (ZP-6 or Pic-SCT)

Pic-SCT was synthesized by a procedure similar to that described for Nic-SCT. Picolinic acid ($3.7 \times 10^{-5}$ mol) was coupled to the deprotected SCT-resin (100 mg) as described above. The Pic-SCT was deprotected and cleaved from the resin using reagent K as described above. The Pic-SCT was purified by HPLC using a linear gradient from 20% to 80% acetonitrile in 20 minutes. The major peak (60% acetonitrile) was collected and lyophilized. The toal amount of peptide was approximately 20 mg. The purified Pic-SCT was then oxidized as generally described for Nic-SCT. The HPLC of the oxidized form showed a single peak, and the retention time (61% acetonitrile) was almost the same as that of the reduced form. The oxidized Pic-SCT was found to be 90% pure based on HPLC (17 mg). The Pic-SCT is further purified by additional HPLC runs.

E. Preparation of 2-Pyrazinoyl-modified calcitonin (ZP-7 or 2-Pyr-SCT)

2-Pyr-SCT was synthesized by a procedure similar to that described for Nic-SCT. 2-Pyranizinecarboxylic acid ($3.7 \times 10^{-5}$ mol) was coupled to the deprotected SCT-resin (100 mg) as described above. The 2-Pyr-SCT was deprotected and cleaved from the resin using reagent K as described above. The 2-Pyr-SCT was purified by HPLC using a linear gradient from 20% to 80% acetonitrile in 20 minutes. The major peak (59% acetonitrile) was collected and lyophilized. The total amount of peptide was approximately 20 mg. The purified 2-Pyr-SCT was then oxidized as generally described for Nic-SCT. The HPLC of the oxidized form showed a single peak, and the retention time (61% acetonitrile) was slightly longer than that of the reduced form. The oxidized 2-Pyr-SCT was found to be >95% pure based on HPLC (18 mg).

F. Preparation of Additional Modified Calcitonins 2,2'-bipyridine-5,5'-dicarboxylic acid (ZP-2 or $Bp_{5,5}$-SCT), 4-4'-biphenyldicarboxylic acid (ZP-3 or BPhe-SCT), isonipecotic acid (ZP-8 or isonip-SCT), DL-pipecolinic acid (ZP-9 or pip-SCT) and nipecotic acid (ZP-10 or nip-SCT) modified salmon calcitonins were synthesized by procedures essentially the same as that described for Nic-SCT. The compounds were purified by HPLC as described above and assayed as described below.

EXAMPLE 2

Characterization on $BP_{4,4}$-CT: Ability to Bind Calcitonin Receptor

The ability of the derivatized $BP_{4,4}$-CT molecule to bind the calcitonin receptor was assayed by measuring the ability of the molecule to increase levels of cyclic AMP in mammalian cells expressing either a recombinant human calcitonin receptor or an endogenous hamster calcitonin receptor.

The human calcitonin receptor was prepared as follows: A plasmid, designated pHOLLEX (deposited as an *E. coli* strain XL-1 blue transformant with the American Type Culture Collection (12301 Parklawn Dr., Rockville, Md.) on Sep. 1, 1992 under accession number 69067), containing a DNA construct capable of directing the expression of a human calcitonin receptor was used to transfect cell line BHK/KZ10-20-48 (as disclosed in copending U.S. patent application Ser. No. 07/954,804, which is incorporated herein in its entirety). BHK/KZ10-20-48 is a BHK cell line transfected with a plasmid containing a luciferase gene whose expression is dependent upon a cyclic AMP response element (CRE), which induces expression of downstream coding sequences in the presence of cyclic AMP. Thus, stimulation of the cyclic AMP pathway, for example by the binding of ligand to the calcitonin receptor, results in expression of the luciferase gene. The vector without the calcitonin receptor was used to transfect the cell line BHK/KZ10-20-48 for a negative control. The transfectants were grown in a selective growth medium (Dulbecco's Modified Eagle Medium (DMEM) with 5% serum) containing both 500 μg/ml G418-neomycin and 250 nM methotrexate.

A BHK cell line expressing the endogenous hamster calcitonin receptor was transfected with plasmid KZ10-20-48 to provide the CRE-inducible luciferase receptor described above. The transfected cells were cultured in selective growth medium containing both 500 μg/mL G418-neomycin and 250 nM methotrexate.

Cells expressing the calcitonin receptor were assayed in triplicate for the induction of the CRE-linked luciferase response to salmon calcitonin (SCT) and derivatized calcitonins at concentrations ranging from $10^{-13}$M to $10^{-6}$M. MICROLITE flat bottom tissue culture plates (Baxter Scientific Products, Chicago, Ill.) were set up such that each well contained $2\times10^4$ cells in 100 μl of selection media, and the cells were grown overnight. SCT and GF43 were prepared at 2X the final assay concentration to give $10^{-13}$ to $10^{-6}$M in growth medium. Induction was initiated by removing old medium from the wells and adding 100 μl of fresh growth medium and 100 μl of either 2X solution in triplicate sample wells. Uninduced luciferase levels were determined in triplicate wells to which 100 μl of DMEM containing 10% fetal calf serum was added. The plates were incubated for four hours at 37° C., 5% $CO_2$ to allow induction of luciferase. Following induction, the media were removed, and the wells were washed once with 200 μl/well PBS. After the wash, 20 μl of a 1:5 dilution (in sterile water) of the stock Cell Culture Lysis Reagent (Luciferase Assay System, Promega Corp., Madison, Wis.) was added to each well, and the plates were incubated for 15 minutes at room temperature. The plates were transferred to a Labsystems Luminoskan microtiter luminometer (Labsystems Inc., Morton Grove, Ill.) which added 40 μl of Luciferase Assay Substrate (Luciferase Assay System, Promega), mixed the reaction for three seconds and integrated the luciferase signal for two seconds per well. The fold induction of luciferase for each compound was calculated as follows:

Fold induction=Induced signal−Uninduced signal Uninduced signal

Results of the assays are summarized in the Table.

TABLE

| Hamster CT receptor | HCT | ZP-1 | ZP-2 | ZP-3 | ZP-5 | ZP-6 | ZP-7 | ZP-8 | ZP-9 | ZP-10 |
|---|---|---|---|---|---|---|---|---|---|---|
| % SCT EC50 | 5.9 × $10^3$ | 73 | 125 | 341 | 71 | 98 | 155 | 106 | 147 | 152 |
| Human CT receptor | HCT | ZP-1 | ZP-2 | ZP-3 | ZP-5 | ZP-6 | ZP-7 | ZP-8 | ZP-9 | ZP-10 |
| % SCT EC50 | 345 | 97 | 199 | 450 | 112 | 140 | 158 | 146 | 230 | 243 |

These data show that derivatized calcitonins ZP-1, ZP-2, ZP-5, ZP-6, ZP-7, ZP-8, ZP-9 and ZP-10 have an EC50 (half maximal activity) similar to salmon calcitonin and have greater activity than human calcitonin. ZP-3 has potency similar to human calcitonin.

EXAMPLE 3

In vivo Effects of BP-CT on Serum Calcium Levels

The biological activity of bipyridine-calcitonin in vivo was measured as the ability of $BP_{4,4}$-CT to lower serum calcium in mice as compared to the action of salmon calcitonin. Six-week old Swiss-Webster male mice (12 to 18 grams) were given single, subcutaneous injections of $BP_{4,4}$-CT, salmon calcitonin or vehicle. Blood samples for serum calcium measurements were collected from orbital sinus punctures at timed intervals of 0, 1 and 4 hours after injection. Serum calcium was analyzed using a Dacos Excel Analyzer (Coulter Electronics Company, Hialeah, Fla.). The compounds were given at the following doses with eight mice randomly assigned to each of the following groups:

| Group No. | Dose |
|---|---|
| 1 vehicle | 0.9% saline |
| 2 BP-CT | 100 ng/ml |
| 3 BP-CT | 1 μg/ml |
| 4 BP-CT | 10 μg/ml |
| 5 SCT | 100 ng/ml |
| 6 SCT | 1 μg/ml |
| 7 SCT | 10 μg/ml |

Figure 1:
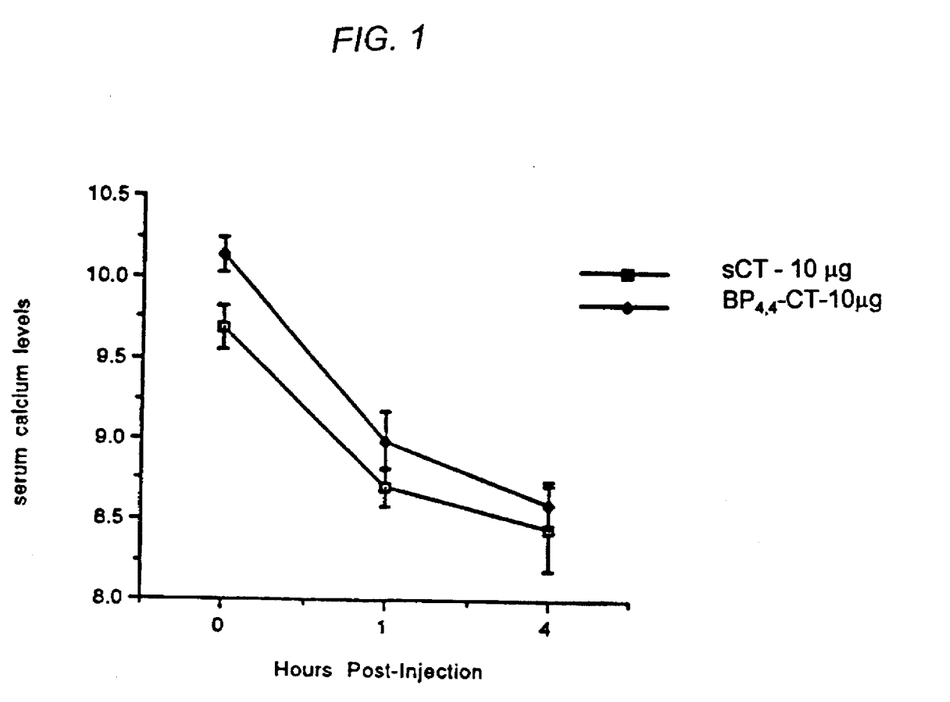
FIGS. 1 and 2 represent the results of an assay measuring serum calcium levels using a compound that is representative of the present invention. $BP_{4,4}$-CT (ZP-1) is the derivatized calcitonin compound and SCT is salmon calcitonin.
Figure 2A:
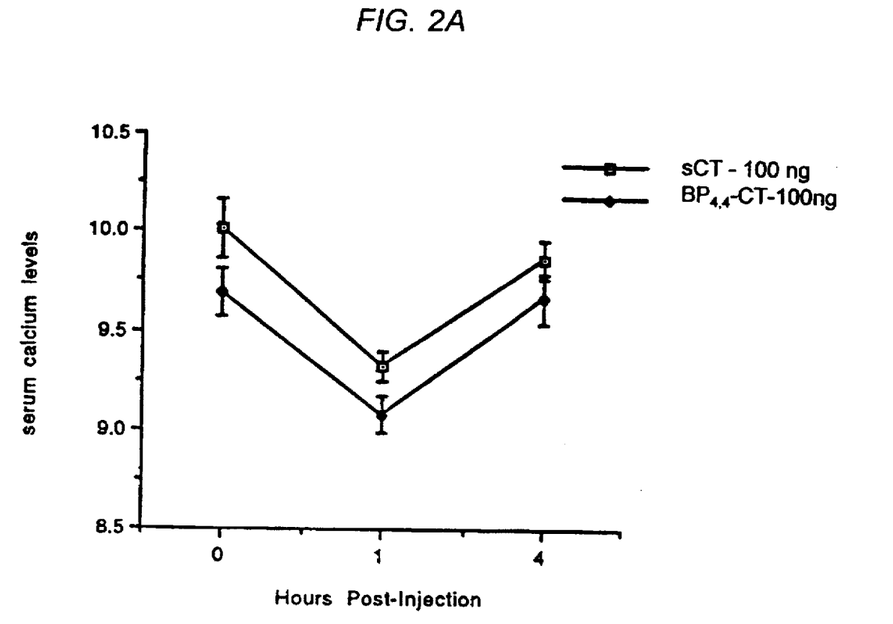
Figure 2B:
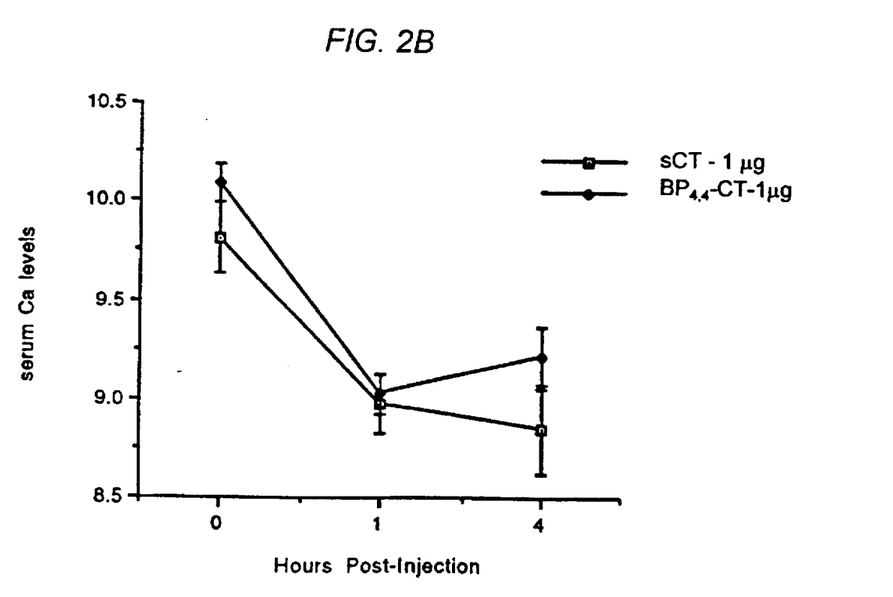

FIGS. 1 and 2 demonstrate that equivalent amounts of $BP_{4,4}$-CT and salmon calcitonin equally decreased serum calcium levels in a dose-dependent manner.

Although certain embodiments of the invention have been described in detail for purposes of illustration, it will be readily apparent to those skilled in the art that the compositions and methods described herein may be modified without departing from the spirit and scope of the invention. Accordingly, the invention is not limited except as by the appended claims.

We claim:

1. A compound selected from the group consisting of:

```
     S―――――――――S
     |         |
R-CONH-Cys-Gly-Asn-Leu-Ser-Thr-Cys-Met-Leu-Gly-Thr-Tyr-Thr-
Gln-Asp-Phe-Asn-Lys-Phe-His-Thr-Phe-Pro-Gln-Thr-Ala-Ile-
Gly-Val-Gly-Ala-Pro-NH₂ (Sequence ID Number 1);
```

```
     S―――――――――S
     |         |
R-CONH-Cys-Ser-Asn-Leu-Ser-Thr-Cys-Val-Leu-Gly-Lys-Leu-Ser-
Gln-Glu-Leu-His-Lys-Leu-Gln-Thr-Tyr-Pro-Arg-Thr-Asn-Thr-
Gly-Ser-Gly-Thr-Pro-NH₂ (Sequence ID Number 2);
``` and pharmaceutically acceptable salts thereof, wherein R is substituted or unsubstituted biaryl, optionally containing 1 or 2 ring nitrogen atoms per ring; or substituted or unsubstituted bis-heterocycloalkyl containing 1 or 2 heteroatoms per ring selected from the group consisting of N, S and O.

2. A compound according to claim 1, wherein R is:

wherein $X_1$ and $Y_1$ are individually C or N; or wherein $X_3$ and $Y_3$ are individually N, O or S; wherein R' is linear $C_1$–$C_8$ alkyl, branched $C_1$–$C_{12}$ alkyl, nitro, hydroxyl, trifluoromethyl, carboxyl, carboxylamide, sulfhydryl, cyano, halo, alkoxy, ester or H.

3. A compound according to claim 2, wherein R is:

4. A compound according to claim 3, wherein R' is $CO_2H$ or H.

5. A compound according to claim 1 wherein R is wherein R' is $CO_2H$ or H.

6. A compound according to claim 1 wherein R is a fused ring structure containing two or three rings.

7. A compound according to claim 1 wherein R is selected from the group consisting of:

8. Compound of the formula R-N-CT, wherein CT is a calcitonin selected from the group consisting of human, salmon, eel, rat, porcine, bovine, ovine and chicken calcitonins and biologically active derivatives and variants thereof, or a pharmaceutically acceptable salt thereof; N is an amide linkage; and wherein R is substituted or unsubstituted biaryl, optionally containing 1 or 2 ring nitrogen atoms per ring; or substituted or unsubstituted bis-heterocycloalkyl containing 1 or 2 heteroatoms per ring selected from the group consisting of N, S and O.

9. A compound according to claim 8 wherein R is:

wherein $X_1$ and $Y_1$ are individually C or N; or wherein $X_3$ and $Y_3$ are individually N, O or S;

wherein R' is linear $C_1$–$C_8$ alkyl, branched $C_1$–$C_{12}$ alkyl, nitro, hydroxyl, trifluoromethyl, carboxyl, carboxylamide, sulfhydryl, cyano, halo, alkoxy, ester or H.

10. A compound according to claim 9 wherein R is:

11. A compound according to claim 10, wherein R' is $CO_2H$ or H.

12. A compound according to claim 8 wherein CT is human or salmon calcitonin.

13. A compound according to claim 10 wherein R is wherein R' is $CO_2H$ or H.

14. A compound according to claim 8 wherein R is a biaryl and each aryl group of the biaryl is a fused ring structure containing two or three rings.

15. A compound according to claim 8 wherein R is selected from the group consisting of:

16. A compound of the formula

X-(R-N-CT)$_n$ wherein X is a monovalent, divalent or trivalent ion of a transition metal; R is a heterocycloalkyl or heteroaryl group; CT is a calcitonin selected from the group consisting of human, salmon, eel, rat, porcine, bovine, ovine and chicken calcitonins and biologically active derivatives and variants thereof; N is an amide linkage; and n=2 or 3; or a pharmaceutically acceptable salt thereof.

17. A compound according to claim 16 wherein X is Fe$^{2+}$.

18. A compound according to claim 16 wherein n=3.

19. A compound according to claim 16 wherein CT is human or salmon calcitonin.

20. A compound according to claim 19 wherein R is wherein R' is CO$_2$H or H.

21. A compound according to claim 16 wherein R is:

wherein R' is CO$_2$H or H.

22. A compound according to claim 16 wherein X is Fe$^{2+}$, R is

CT is human or salmon calcitonin, and n=3.

23. A compound according to claim 16 wherein R is selected from the group consisting of:

24. A compound according to claim 16 wherein R is a fused ring structure containing two or three rings.

25. A pharmaceutical composition comprising a compound according to claim 8 and a pharmaceutically acceptable carrier.

26. A method of reducing serum calcium in a patient, comprising administering to said patient an effective amount of a pharmaceutical composition comprising a compound according to claim 8 and a pharmaceutically acceptable carrier.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 32 amino acids
      ( B ) TYPE: amino acid
      ( D ) TOPOLOGY: linear ( i x ) FEATURE:
      ( A ) NAME/KEY: Modified-site
      ( B ) LOCATION: 32
      ( D ) OTHER INFORMATION: /label=amidated
         / note="C-terminal proline residue is amidated"

( x i ) SEQUENCE DESCRIPTION: SEQ ID NO:1:

```
Cys Gly Asn Leu Ser Thr Cys Met Leu Gly Thr Tyr Thr Gln Asp Phe
 1               5                  10                 15

Asn Lys Phe His Thr Phe Pro Gln Thr Ala Ile Gly Val Gly Ala Pro
             20                  25                 30
```

( 2 ) INFORMATION FOR SEQ ID NO:2:

( i ) SEQUENCE CHARACTERISTICS:
      ( A ) LENGTH: 32 amino acids
      ( B ) TYPE: amino acid
      ( D ) TOPOLOGY: linear ( i x ) FEATURE:
      ( A ) NAME/KEY: Modified-site
      ( B ) LOCATION: 32
      ( D ) OTHER INFORMATION: /label=amidated
         / note="C-terminal Proline residue is amidated."

( x i ) SEQUENCE DESCRIPTION: SEQ ID NO:2:

```
Cys Ser Asn Leu Ser Thr Cys Val Leu Gly Lys Leu Ser Gln Glu Leu
 1               5                  10                 15

His Lys Leu Gln Thr Tyr Pro Arg Thr Asn Thr Gly Ser Gly Thr Pro
             20                  25                 30
```